United States Patent [19]
Cropp

[11] Patent Number: 5,948,799
[45] Date of Patent: Sep. 7, 1999

[54] METHOD FOR IMPROVING MORBIDITY AND/OR MORTALITY

[75] Inventor: Anne Barbara Cropp, Madison, Conn.

[73] Assignee: Pfizer Inc., New York, N.Y.

[21] Appl. No.: 08/815,528

[22] Filed: Mar. 12, 1997

Related U.S. Application Data

[60] Provisional application No. 60/013,593, Mar. 15, 1996.

[51] Int. Cl.$^6$ ...................................... A61K 38/55
[52] U.S. Cl. ................... 514/356; 514/222.5; 514/223.8; 514/247; 514/249; 514/255; 514/258; 514/349; 514/869
[58] Field of Search ................................. 514/356, 222.5, 514/223.8, 247, 249, 255, 258, 349, 869

[56] References Cited

U.S. PATENT DOCUMENTS 5,098,910   3/1992   Becker et al. .
5,155,120  10/1992   Lazar et al. .............................. 514/356

FOREIGN PATENT DOCUMENTS 9628185   9/1996   WIPO .

OTHER PUBLICATIONS

Sun, J. X. et al., European Journal of Clinical Pharmacology, vol. 47, No. 3, 1994, pp. 285–289.
Packer, M. et al., Supplement to Journal of the American College of Cardiology, vol. 17, No. 2, Supplement A, 274A, Mar. 6, 1991, 2:30 p.m.
Cohn, J. N., Drugs, vol. 47, Supplement 4, 1994, pp. 47–58.
Elkayam, U. et al., Supplement to Journal of the American College of Cardiology, vol. 22, No. 4, Oct. 1993: 139A–144A.
Singh, S. et al., The New England Journal of Medicine, vol. 333, No. 2, Jul. 13, 1995, pp. 77–82.
Packer, M. et al., The New England Journal of Medicine, vol. 335, No. 15, Oct. 10, 1996, pp. 1107–1114.
CIBIS Investigators and Committees, The Cardiac Insufficiency Bisoprolol Study (CIBIS), Circulation vol. 90, No. 4, Oct. 1994, pp. 1765–1773.

*Primary Examiner*—Frederick Krass
*Attorney, Agent, or Firm*—Peter C. Richardson; Gregg C. Benson; Jennifer A. Kispert

[57] ABSTRACT

This invention relates to a method for reducing morbidity and/or mortality in a mammal with congestive heart failure due to non-ischemic etiology comprising administering amlodipine or a pharmaceutically acceptable amlodipine acid addition salt, and, optionally, a diuretic and/or digoxin. The invention further relates to methods for treating patients with congestive heart failure due to non-ischemic etiology, comprising administering a non-ischemic congestive heart failure treating amount of amlodipine or a pharmaceutically acceptable amlodipine salt and, optionally, a diuretic and/or digoxin. The invention also provides a kit which comprises a container means and a) amlodipine and a diuretic, b) amlodipine and digoxin, or c) amlodipine, digoxin and a diuretic; and a kit which comprises a container means and a) amlodipine, an angiotensin converting enzyme (ACE) inhibitor and a diuretic, b) amlodipine, an ACE inhibitor and digoxin, or c) amlodipine, an ACE inhibitor, digoxin and a diuretic. Further, this invention relates to compositions comprising amlodipine or a pharmaceutically acceptable salt thereof and one or both of digoxin and/or a diuretic.

10 Claims, No Drawings

METHOD FOR IMPROVING MORBIDITY AND/OR MORTALITY

CROSS REFERENCE TO RELATED APPLICATION

This application is a nonprovisional application claiming benefit of provisional application No. 60/013,593, filed Mar. 15, 1996.

FIELD OF THE INVENTION

This invention relates to: a method for reducing morbidity and/or mortality in a mammal with congestive heart failure due to non-ischemic etiology comprising administering amlodipine or a pharmaceutically acceptable amlodipine acid addition salt, and, optionally, a diuretic and/or digoxin; methods for treating patients with congestive heart failure due to non-ischemic etiology, comprising administering a non-ischemic congestive heart failure treating amount of amlodipine or a pharmaceutically acceptable amlodipine salt and, optionally, a diuretic and/or digoxin; compositions comprising a) amlodipine and a diuretic, b) amlodipine and digoxin, or c) amlodipine, digoxin and a diuretic; a kit which comprises a container means and a) amlodipine and a diuretic, b) amlodipine and digoxin, or c) amlodipine, digoxin and a diuretic; and a kit which comprises a container means and a) amlodipine, an angiotensin converting enzyme (ACE) inhibitor and a diuretic, b) amlodipine, an ACE inhibitor and digoxin, or c) amlodipine, an ACE inhibitor, digoxin and a diuretic.

BACKGROUND OF THE INVENTION

Congestive heart failure, regardless of its etiology, is characterized by a weakness of the myocardial tissue of the left and/or right ventricle of the heart to pump and thereby circulate blood into systemic and/or pulmonary circulations. It is accompanied by circulatory and neurohumoral changes which result in failure to deliver sufficient blood and oxygen supply to peripheral tissues and vital organs. If left untreated, the health of a patient with congestive heart failure could progress to the point where the disease would be fatal.

Survival data from patients with overt congestive heart failure in the Framingham Heart Study indicate persisting high lethality without significant temporal prognostic improvement during the 40 year period 1948–1988 (Ho K K L, Anderson K M, Kannel W B, Grossman W, Levy D. Survival after the onset of congestive heart failure in Framingham Heart Study subjects. Circulation 1993; 88: 107–115). Over the years a precise definition of heart failure has remained elusive. Heart failure is generally characterized by an inadequacy of the heart, usually in association with elevated central cardiac filling pressures, to meet the metabolic demands of peripheral organs and tissues either at rest or during stress. The lack of a uniformly accepted definition of heart failure and the myriad of patient subsets within this heterogenous diagnosis present a considerable challenge to the practicing physician selecting therapy.

The term "cardiomyopathy" is used to define diseases of the myocardium of either known or unknown etiology. In approximately 75–80% of heart failure patients coronary artery disease is the underlying cause and is designated "ischemic cardiomyopathy". Table 1 lists most of the etiologies and associations of cardiomyopathy that are not attributed to underlying coronary artery disease (CAD), and are designated "non-ischemic cardiomyopathies".

TABLE 1

Non-Ischemic Causes of Cardiomyopathy

| | |
|---|---|
| 1) Idiopathic | 8) Infectious (Viral, bacterial, rickettsial, Protozoal) |
| 2) Granulomatous disease (Idiopathic, Sarcoidosis, Giant cell, Wegner's) | 9) Metabolic/endocrine (Acromegaly, Hypothyroidism, Pheochromocytoma, diabetes, beriberi, selenium deficiency, Kwashiorkor, hemochromatosis, thiamine deficiency) |
| 3) Collagen vascular disease (Lupus ethythematosus, dermatomyositis) | |
| 4) Neuromuscular disease | |
| 5) Hypertension | 10) Polyarteritis nodosa (Scleroderma) |
| 6) Cardiac valvular disease | 11) Toxins (alcohol, radiation arsenic, cobalt, lead, carbon tetrachloride, carbon monoxide, amphetamines, cocaine, anthracyclines, cyclophosphamide) |
| 7) Genetic or familial cardiomyopathy | |
| | 12) Peri- or Post-partum cardiomyopathy |
| | 13) Allergic or hypersensitivity |
| | 14) Myocarditis |

The underlying cause of cardiomyopathy rather than the severity of the heart failure syndrome may influence the response to drug therapy. Some evidence exists to suggest that preferential benefit accrues to patients with non-ischemic cardiomyopathy as opposed to those with heart failure due to coronary artery disease. In the Veterans Affairs Survival Trial of Antiarrhythmic Therapy in Congestive Heart Failure only patients with heart failure not due to myocardial ischemia seemed to derive a benefit from amiodarone, a class III antiarrhythmic compound with beta-blocking properties. (Singh S N, Fletcher R D, Gross Fisher S, et al. Amiodarone in patients with congestive heart failure and asymptomatic ventricular arrhythmia. N Engl J Med 1995; 333: 77–82). Similarly, another trial using the beta blocker bisoprolol, Cardiac Insufficiency Bisoprolol Study (CIBIS), found no significant risk reduction in patients with ischemic heart failure but did find a benefit in those with non-ischemic heart failure. (CIBIS Investigators and Committees. A randomized trial of Beta blockade in heart failure: the Cardiac Insufficiency bisoprolol Study (CIBIS). Circulation 1994; 90: 1765–73).

Amlodipine, 3-ethyl-5-methyl-2-(2-aminoethoxymethyl) 4-(2-chlorophenyl)-1,4-dihydro-6-methylpyridine-3,5-dicarboxylate, see U.S. Pat. No. 4,572,909, and its pharmaceutically acceptable acid addition salts are calcium channel blockers known for their effectiveness in the treatment, inter alia, of congestive heart failure, see U. S. Pat. No. 5,155,120 to Lazar et al. Amlodipine is currently marketed as the besylate salt, see U.S. Pat. No. 4,879,303. The teachings of U.S. Pat. Nos. 4,572,909, 4,879,303 and 5,155,120 are incorporated herein by reference.

ACE inhibitors are well known in the art for their activity in inhibiting angiotensin converting enzyme, thereby blocking conversion of the decapeptide angiotensin I to angiotensin II. The principal pharmacological and clinical effects of ACE inhibitors arise from suppression of synthesis of angiotensin II. Angiotensin II is a potent pressor substance and, therefore, blood pressure lowering can result from inhibition of its biosynthesis, especially in animals and humans whose hypertension is angiotensin II related. ACE inhibitors are effective antihypertensive agents in a variety of animal models and are clinically useful for the treatment of hypertension in humans.

ACE inhibitors are also employed for the treatment of heart conditions such as hypertension and heart failure. It is known that at least some ACE inhibitors can improve (i.e., decrease) morbidity and mortality in patient populations with heart conditions.

International application PCT/US92/03873, published as WO 92/20342, discloses pharmaceutical compositions containing a combination of an angiotensin II antagonist and a calcium channel blocker for use in the treatment of hypertension and congestive heart failure. The publication states that the particular compositions can further contain antihypertensives and/or diuretics and/or angiotensin converting enzyme inhibitors.

U.S. patent application Ser. No. 08/405,108 filed Mar. 16, 1995, abandoned in favor of International PCT Application No. PCT/IB96/00145 filed Feb. 26, 1996 published as WO 96/28185, now U.S. patent application Ser. No. 08/894,800 by the instant inventor and assigned to the assignee hereof, discloses a composition comprising amlodipine, a pharmaceutically acceptable salt of amlodipine or felodipine and an ACE inhibitor and, optionally, a diuretic and/or digoxin; a method for reducing morbidity and/or mortality in a mammal with congestive heart failure; and a method for treating congestive heart failure, both methods comprising administering a combination of amlodipine, a pharmaceutically acceptable salt of amlodipine or felodipine and ACE inhibitor and, optionally, a diuretic and/or digoxin.

SUMMARY OF THE INVENTION

This invention provides methods for reducing morbidity and/or mortality in a mammal with congestive heart failure due to non-ischemic etiology, comprising administering to a mammal, especially a human, in need of such treatment a non-ischemic congestive heart failure treating amount of a compound selected from the group consisting of amlodipine and pharmaceutically acceptable salts of amlodipine.

The immediately foregoing method for reducing morbidity and/or mortality may optionally comprise the co-administration of digoxin and/or a diuretic. Preferably, the diuretic is selected from the group consisting of methyclothiazide, hydrochlorothiazide, torsemide, metolazone, furosemide, chlorthalidone, N-(5-sulfamoyl-1, 3,4-thiadiazol-2-yl) acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

The foregoing methods for reducing morbidity and/or mortality in a mammal with congestive heart failure due to non-ischemic etiology, is preferably administered for longer than 16 weeks and is especially preferably administered for longer than six months.

Further, this invention provides a method for treating congestive heart failure due to non-ischemic etiology in a mammal comprising administering, to a mammal in need of such treatment, a non-ischemic congestive heart failure treating amount of a compound selected from the group consisting of amlodipine and pharmaceutically acceptable salts of amlodipine.

The immediately foregoing method for treating congestive heart failure due to non-ischemic etiology may optionally comprise the co-administration of digoxin and/or a diuretic. Preferably, the diuretic is selected from the group consisting of methyclothiazide, hydrochlorothiazide, torsemide, metolazone, furosemide, chlorthalidone, N-(5-sulfamoyl-1,3,4-thiadiazol-2-yl)acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

The foregoing methods for treating congestive heart failure due to non-ischemic etiology, is preferably administered for longer than 16 weeks and is especially preferably administered for longer than six months.

This invention also provides compositions comprising amlodipine and one or both of digoxin and/or a diuretic. Preferably the diuretic is selected from the group consisting of methyclothiazide, hydrochlorothiazide, torsemide, metolazone, furosemide, chlorthalidone, N-(5-sulfamoyl-1, 3,4-thiadiazol-2-yl)acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

The besylate salt of amlodipine is preferred in all of the methods and compositions described herein.

This invention also provides a kit containing a treatment for reducing morbidity and/or mortality in a mammal with congestive heart failure regardless of etiology or for treating a mammal with congestive heart failure regardless of etiology, comprising a therapeutically effective amount of amlodipine or a pharmaceutically acceptable salt of amlodipine and a pharmaceutically acceptable carrier in a first unit dosage form and, optionally, a) a therapeutically effective amount of a diuretic and a pharmaceutically acceptable carrier in a second unit dosage form; and/or b) a therapeutically effective amount of digoxin and a pharmaceutically acceptable carrier in a third unit dosage form; and a container means for containing said first unit dosage form and one or both of said second unit dosage form and/or said third unit dosage form. Preferably, the diuretic in the kit is selected from the group consisting of methyclothiazide, hydrochlorothiazide,torsemide, metolazone, furosemide, chlorthalidone, N-(5-sulfamoyl-1,3,4-thiadiazol-2-yl) acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid. More preferably, the first unit dosage form comprises the besylate salt of amlodipine.

This invention further provides a kit containing a treatment for reducing morbidity and/or mortality in a mammal with congestive heart failure regardless of etiology or for treating a mammal with congestive heart failure regardless of etiology, comprising a therapeutically effective amount of amlodipine or a pharmaceutically acceptable salt of amlodipine and a pharmaceutically acceptable carrier in a first unit dosage form; a therapeutically effective amount of an ACE inhibitor and a pharmaceutically acceptable carrier in a second unit dosage form; and, optionally, a therapeutically effective amount of a diuretic and a pharmaceutically acceptable carrier in a third unit dosage form; and/or a therapeutically effective amount of digoxin and a pharmaceutically acceptable carrier in a fourth unit dosage form (however, the designation of a diuretic as a "third unit dosage form" and digoxin as "a fourth unit dosage form" are not to be taken as absolute designations since if the kit comprises three unit dosage forms and digoxin is one of the three in the kit then digoxin will be designated as the "third unit dosage form"); and a container means for containing said first and second unit dosage forms and, optionally, said third unit dosage form and/or said fourth unit dosage form. The ACE inhibitor in the instant kit is preferably selected from the group consisting of captopril, enalapril, enalaprilat, fosinopril sodium, lisinopril, pentopril, perindopril, quinapril hydrochloride, quinaprilat, ramipril, ramiprilat, trandolapril and zofenopril calcium or the ACE inhibitor is benazepril. Preferably, the diuretic in the instant kit is selected from the group consisting of methyclothiazide, hydrochlorothiazide, torsemide, metolazone, furosemide, chlorthalidone, N-(5-sulfamoyl-1,3,4-thiadiazol-2-yl) acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid. More preferably, the first unit dosage form comprises the besylate salt of amlodipine.

The phrase "with congestive heart failure" includes patients who are at risk of suffering from this condition relative to the general population, even though they may not have suffered from it yet, by virtue of exhibiting risk factors. For example, a patient with untreated hypertension may not have suffered from congestive heart failure, but is at risk because of his or her hypertensive condition.

The term "treating", "treat" or "treatment" as used herein includes preventative (e.g., prophylactic) and palliative treatment.

The method referred to above for reducing morbidity and/or mortality generally refers to benefits and/or survival in the long term. Clinical benefits may be observable within a few weeks, for example 2–3 weeks, however, this does not imply that the patients are not benefiting from the treatment prior to actual clinical observation. It is preferred, however that administration be effected long term; that is for longer than 16 weeks, and preferably longer than 6 months.

Other components may also be optionally included as part of the compositions administered in the methods of this invention. When included, such optional components will generally include digoxin and/or a diuretic. As known in the art, digoxin is a glycoside obtained from the leaves of digitalis. Other forms of digitalis exist, although digoxin is the form usually employed throughout the medical profession.

"Co-administration" of a combination of amlodipine (or its salts) and/or a diuretic and/or digoxin (as long as one of digoxin or a diuretic is administered with amlodipine or its salts) means that these components can be administered together as a composition or as part of the same, unitary dosage form. "Co-administration" also includes administering amlodipine and/or a diuretic and/or digoxin separately but as part of the same therapeutic treatment program or regimen. The components need not necessarily be administered at essentially the same time, although they can if so desired. Thus "co-administration" includes, for example, administering amlodipine and/or a diuretic and/or digoxin as separate dosages or dosage forms, but at the same time. "Co-administration" also includes separate administration at different times and in any order. For example, where appropriate a patient may take one or more component(s) of the treatment in the morning and the one or more of the other component(s) at night.

This invention is surprising because, as demonstrated by the clinical studies disclosed below, amlodipine decreases the morbidity and/or mortality of a patient population with congestive heart failure due to non-ischemic etiology over and above that which can be attributed to the combination of ACE inhibitors, digoxin and a diuretic. This result is surprising because, although ACE inhibitors are known to be capable of improving morbidity and/or mortality in patients with congestive heart failure, calcium channel blockers are not heretofore known to produce such a desirable effect.

DETAILED DESCRIPTION

A diuretic may optionally be included as part of the therapeutic regimen and may similarly be widely selected from among those conventionally known in the art. Useful diuretics include methyclothiazide, hydrochlorothiazide, torsemide, metolazone, furosemide, chlorthalidone, N-(5-sulfamoyl-1,3,4-thiadiazol-2-yl)acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

The active ingredient (amlodipine or a salt thereof) can be administered orally in solid dosage forms such as capsules, tablets, and powders, or in liquid dosage forms such as elixirs, syrups, and suspensions. It can also be administered parenterally, together or separately, in sterile liquid dosage forms.

Gelatin capsules can also be made conventionally to contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration, for example, intravenously, intramuscularly or subcutaneously, can contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents, also are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

Although the generic name of amlodipine represents the free base, amlodipine can also be used in the form of a pharmaceutically acceptable acid addition salt, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methanesulfonate, ethanesulfonate, benzenesulfonate, or p-toluenesulfonate. Preferred is the besylate salt as disclosed in U.S. Pat. No. 4,879,303, the teachings of which are incorporated herein by reference.

The various active components comprising amlodipine or a pharmaceutically acceptable amlodipine salt and, optionally, digoxin and/or a diuretic will each be co-administered in amounts effective to treat congestive heart failure due to non-ischemic etiology, said amounts being sufficient to decrease morbidity and mortality in a population of patients suffering or at risk of suffering from congestive heart failure due to non-ischemic etiology. The amount of amlodipine administered will generally be 1–20 mg daily, preferably 5–10 mg daily when administered orally. The dose can be divided if desired, although no particular therapeutic advantage is seen in doing so.

A diuretic which may optionally also be employed may be administered in an amount which varies according to the particular compound employed, but which will generally be within the amount generally known for the diuretic when administered alone. Table 2 below gives typical and preferred oral dosage ranges for use in the invention for a number of well known diuretics.

TABLE 2

DIURETIC DOSAGES

| DIURETIC | TYPICAL RANGE (mg/day) | PREFERRED RANGE (mg/day) |
|---|---|---|
| BENDROFLUMETHIAZIDE | 1.25 mg–40 mg | 2.5 mg–20 mg |
| BENZTHIAZIDE | 3.125 mg–200 mg | 6.25 mg–100 mg |
| CHLOROTHIAZIDE | 62.5 mg–2000 mg | 1.25 mg–1000 mg |
| HYDROCHOROTHIAZIDE | 6.25 mg–200 mg | 6.25 mg–100 mg |
| HYDROFLUMETHIAZIDE | 6.25 mg–200 mg | 12.5 mg–100 mg |
| POLYTHIAZIDE | 0.25 mg–16 mg | 1 mg–4 mg |
| TRICHLORMETHIAZIDE | 0.25 mg–16 mg | 1 mg–4 mg |
| CHLORTHALIDONE | 6.25 mg–200 mg | 12.5 mg–100 mg |
| INDAPAMIDE | 1.25 mg–20 mg | 2.5 mg–5 mg |
| METOLAZONE | 0.25 mg–30 mg | 0.5 mg–15 mg |
| QUINETHAZONE | 25 mg–200 mg | 50 mg–100 mg |
| BUMETANIDE | 0.25 mg–40 mg | 0.5 mg–20 mg |
| ETHACRYNIC ACID | 12.5 mg–400 mg | 25 mg–200 mg |
| FUROSEMIDE | 5 mg–2000 mg | 10 mg–200 mg |
| TORSEMIDE | 2.5 mg–500 mg | 5 mg–300 mg |
| AMILORIDE | 2.5 mg–30 mg | 5 mg–10 mg |
| SPIRONOLACTONE | 12.5 mg–400 mg | 25 mg–200 mg |
| TRIAMTERENE | 12.5 mg–400 mg | 25 mg–200 mg |

The dosages for the various active ingredients will generally be somewhat lower than previously disclosed if administration is parenteral.

Digoxin, if optionally employed, will be administered in an amount of 0.1 mg daily to 5 mg per week, usually once daily in an amount not exceeding 1 mg.

Of course, the attending physician can generally tailor the dose of each active ingredient in a given case.

U.S. patent application Ser. No. 08/405,108 filed Mar. 16, 1995, abandoned in favor of International PCT Application No. PCT/IB96/00145 filed Feb. 26, 1996 published as WO 96/28185, now U.S. patent application Ser. No. 08/894,800 by the instant inventor and assigned to the assignee hereof, discloses that the combination of amlodipine or a pharmaceutically acceptable salt of amlodipine and an ACE inhibitor and, optionally, a diuretic and/or digoxin may be co-administered in amounts effective to reduce morbidity and/or mortality in a mammal with congestive heart failure regardless of etiology or to treat congestive heart failure regardless of etiology, said amounts being sufficient to decrease morbidity and mortality in a population of patients at risk of suffering from congestive heart failure. As demonstrated by clinical studies, the combination of amlodipine and an ACE inhibitor decreases the morbidity and/or mortality of a patient population with congestive heart failure over and above that which can be attributed to an ACE inhibitor alone. The amount of amlodipine co-administered will generally be 1–20 mg daily, preferably 5–10 mg daily when administered orally. The dose can be divided if desired, although no particular therapeutic advantage is seen in doing so.

The ACE inhibitor will be co-administered in an amount which varies according to the particular compound employed, but which will generally be within the amount generally known for the inhibitor when administered alone. Table 3 below gives typical and preferred oral dosage ranges for a number of well known ACE inhibitors.

TABLE 3

ACE INHIBITORS

| NAME | TYPICAL RANGE (mg/day) | PREFERRED RANGE (mg/day) |
|---|---|---|
| CAPTOPRIL | 1 mg–150 mg | 3.125 mg–40 mg |
| ENALAPRIL | 0.75 mg–60 mg | 1.25 mg–40 mg |
| ENALAPRILAT | 0.3 mg–40 mg | 0.3 mg–20 mg |
| FOSINOPRIL | 2.5 mg–160 mg | 5 mg–80 mg |
| LISINOPRIL | 2.5 mg–80 mg | 2.5 mg–40 mg |
| QUINAPRIL | 2.5 mg–120 mg | 5 mg–80 mg |
| BENAZEPRIL | 2.5 mg–160 mg | 2.5 mg–80 mg |
| RAMIPRIL | 0.625 mg–80 mg | 1.25 mg–40 mg |
| TRANDOLAPRIL | 0.125 mg–10 mg | 0.25 mg–6 mg |

The same holds true for the particular diuretic which may optionally also be employed (see Table 2). Digoxin, if optionally co-administered with amlodipine and an ACE inhibitor, will be administered in an amount of 0.1 mg daily to 5 mg per week, usually once daily in an amount not exceeding 1 mg. Of course, the attending physician can generally tailor the dose of each active ingredient in a given case. Thus, this invention also relates to combining separate pharmaceutical compositions of each of amlodipine or a pharmaceutically acceptable salt of amlodipine and an ACE inhibitor and, optionally, a diuretic and/or digoxin in kit form.

A "kit" as used in the instant application includes container means for containing the separate compositions such as a divided bottle or a divided foil packet. The container means can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container means employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a memory aid on a written matter, where the written matter is of the type containing information and/or instructions for the physician, pharmacist or patient, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday, . . . etc . . . . Second Week, Monday, Tuesday, . . ." etc. Other variations of memory aids will be readily apparent. A "daily dose" can be a single tablet or capsule or several pills or capsules to be taken on a given day. Also a daily dose of one or more component(s) of the kit can consist of one tablet or capsule while a daily dose of another one or more components of the kit can consist of several tablets or capsules. The memory aid should reflect this.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The effectiveness of amlodipine in decreasing morbidity and/or mortality was shown by the following clinical study which illustrates the use of amlodipine, employed as the besylate salt in the study. The study was a randomized, double-blind, parallel group, placebo controlled multicenter study investigating the effects of amlodipine therapy on mortality and cardiac events in patients with severe heart failure. Patients entering the trial received background therapy consisting of an ACE inhibitor, digoxin, and diuretic. Investigators were allowed to use a diuretic and ACE inhibitor according to their own choice since the study was intended to represent the usual and customary care of patients. The timing and frequency of administration of the ACE inhibitor and diuretic were not pre-specified and were in keeping with the pharmacodynamic properties of the individual active agents. Amlodipine besylate was administered once daily each morning.

Stratification of patients by heart failure etiology was stipulated in the protocol a priori. Based on medical history patients were randomized into either of two strata, an ischemic stratum or a non-ischemic stratum. Following a screening visit, consenting and qualifying patients were randomly allocated to receive amlodipine or placebo orally in a double-blind fashion for a minimum of six months.

The purpose of the study was to evaluate the effect of amlodipine compared with placebo on combined mortality (cardiac and non-cardiac deaths) and life-threatening cardiac events in patients with severe heart failure.

Patients with chronic heart failure were enrolled at 105 centers. Patients were eligible if they had heart failure for at least 2 months. All patients were symptomatic (i.e., experiencing fatigue, palpitations or dyspnea) at rest, or upon minimal exertion (i.e., walking across a room or down a hallway) despite adequate treatment with ACE inhibitors, digoxin, and diuretics for at least 2 months. Heart failure was predominantly systolic with left ventricular ejection fraction lower than 30%. Patients were excluded if they demonstrated New York Heart Association (NYHA) symptoms within two months of screening, or had a primary valvular or pericardial disorder or obstructive or hypertrophic cardiomyopathy. Patients were also excluded if they had unstable angina or a recent myocardial infarction or cardiac procedure; if they had a history of sustained ventricular arrhythmias or sudden death; or if they were receiving calcium channel antagonists, beta-adrenergic blockers, oral levodopa, cardiodepressant antiarrhythmic drugs (and/or including propafenone, morizicine, sotalol), direct acting vasodilator drugs (although short- and long-acting nitrates were permitted). Patients were also excluded if they had any of the following: systolic blood pressure less than 84 mmHg or greater than 160 mmHg, or diastolic blood pressure greater than 90 mmHg; clinical evidence of digoxin toxicity; second or third degree AV-block not treated with a functional pacemaker; severe primary lung disease or respiratory failure; or any clinically important laboratory abnormality.

Following a baseline evaluation qualifying patients were randomized to double-blind therapy with amlodipine or matching placebo. Randomization was stratified based on whether the patient had coronary artery disease (ischemic cardiomyopathy) as the cause of heart failure. Diagnosis and subsequent randomization to the non-ischemic cardiomyopathy group was one of exclusion. Randomization was stratified based on whether the patient had coronary artery disease (ischemic stratum) as the cause of heart failure. Study medication was dispensed in identically matching amlodipine and placebo tablets with individually coded bottles prepared for each patient. The patients received amlodipine or placebo in a single tablet daily for 2 weeks, after which the dose was increased to two tablets daily, unless the lower dose was not tolerated. For amlodipine this corresponded to 5 mg and then 10 mg daily. Patients were followed every one to 3 months until the completion of the study. Background therapy (ACE-inhibitor, digoxin, and diuretic) was adjusted as clinically indicated. Open-label therapy with amlodipine was not permitted throughout the course of the trial.

The study was endpoint-driven. The primary endpoint was combined risk of cardiac morbidity and all-cause (cardiac and non-cardiac) mortality. A morbid event was considered an endpoint if there was evidence of deterioration of heart failure (acute pulmonary edema or severe hypoperfusion), acute myocardial infarction, or life-threatening ventricular arrhythmia requiring therapy. Separate secondary analyses were performed for all-cause mortality and cardiovascular mortality. All endpoints were adjudicated and deemed final by an independent classification committee blinded to treatment assignment. An independent Data and Safety Monitoring Board (DSMB) was established to monitor the accumulating data for evidence of benefit or harm to patients enrolled in the trial that could have been attributed to one of the treatment arms.

The primary objective of the study, as specified in the original protocol, was to compare the effect of amlodipine with placebo on combined mortality (cardiac and non-cardiac death) and life-threatening cardiovascular events.

Secondary analyses were performed for: 1) all-cause mortality; and 2) cardiovascular mortality. The sample-size for the trial was estimated to be 800, based on the assumption of a one-year combined event rate of 40%. The study was designed to have a power of 90 percent (two-tailed) to detect a difference of 25 percent in event rate between the two treatment groups. Since it was recognized that any estimate of event rate made before the study might be inaccurate, it was planned that the trial should continue until 190 patients receiving placebo had reached a primary endpoint, as deemed by the Data and Safety Monitoring Board. As per protocol, enrollment in the trial continued until a total of 190 events occurred in the placebo group, and then all patients were followed for an additional 6 months. Accrual was extended to 1100 in order to protect against unexpectedly low event rates or poor compliance. A total of 1153 patients were recruited for the study.

Interim statistical analyses were performed at pre-specified times by an independent statistical center in order to monitor patient safety and treatment efficacy. Each interim data safety report presented all aspects of the study from data collected for each patient. The independent Data and Safety Monitoring Board reviewed each interim safety report, with primary emphasis placed on the evaluation of the primary endpoint events, as well as overall mortality. To protect against increasing the rate of false positive errors due to interim analyses, the Lan-DeMets procedure (Biometrika, 70, 659–663, 1983) was applied, with an O'Brien-Fleming (Biometrics, 35, 549–556, 1979) type of boundary. Baseline characteristics for the two treatment groups were compared by the Wilcoxin statistic (for continuous variables) and the chi-square statistic for categorical. Survival curves were constructed by use of the Kaplan-Meier estimate and differences between the curves were tested for significance by the log-rank test. The survival analyses included all randomized patients. All deaths were reported according to the etiology of heart failure (ischemic, non-ischemic) and the intention to treat principle was applied. Differences between treatment groups in events after randomization were analyzed by the t-test or chi-square test, as appropriate.

Of the 1153 patients enrolled in the study, 571 patients were assigned to treatment with amlodipine and 582 to treatment with placebo. A total of 875 male (76%) and 278 female (24%) patients participated in the study. The two treatment groups were similar in all their pre-treatment characteristics, with no notable imbalance between treatment arms with the possible exception of history of antiarrhythmic use being more prevalent on the placebo arm (25%) as compared to the amlodipine arm (20%). Less than two thirds (734, 63.7%) of the patients accrued were of ischemic etiology. Idiopathic cardiomyopathy was the most frequently assigned underlying cause of non-ischemic heart failure (182 amlodipine, 174 placebo). As anticipated, there were fewer NYHA IV patients (222, 19%) than NYHA III (930, 81%). One patient was randomized despite being diagnosed with NYHA II symptoms. Duration of heart failure (mean) in the amlodipine group was 4.1 years and 3.9 years in the placebo group. The median left ventricular ejection fraction and cardiothoracic ratio were 21% and 0.6 respectively, in both treatment groups. The duration of follow-up ranged from 2 to 1008 days (mean 423.0 days) in the amlodipine group and 1 to 982 days (mean 416.4 days) in the placebo group.

The results are summarized as follows.

Primary and Secondary Analyses: During the course of the study there were 468 primary endpoints, 222 events in amlodipine-treated patients, and 246 events in placebo (p=0.30). In the evaluation of all-cause mortality patients treated with amlodipine experienced fewer deaths than those treated with placebo (190 vs. 223, respectively; p=0.07). The data was tested for the presence of interaction effects between etiology (pre-specified stratification) and treatment. A significant interaction between treatment and etiology was detected for the combined primary endpoint (p=0.04) and for all-cause mortality (p=0.004). That is, the effects of treatment were different in the ischemic and non-ischemic subgroups. In such a situation, it is appropriate to base inferences on separate analyses in each subgroup. Conversely, it is statistically questionable to pool the interacting subgroups into a common analysis. Accordingly, treatment effects were examined in the separate etiology strata following conventional statistical procedure. In the ischemic stratum there was no difference in the number of events in the amlodipine and placebo treatment arms for the primary endpoint (164 and 168, respectively; p=0.74). However, in the non-ischemic stratum there were 58 primary endpoints reported in the amlodipine group compared to 78 events in the placebo group, with an overall 31% reduction in the risk (hazard ratio of 0.695) of experiencing a primary endpoint (95% Cl for the hazard ratio 0.494 to 0.976) which was statistically significant (p=0.036). In examining the treatment effect on all-cause mortality in ischemic patients there was no difference between treatment groups (p=0.8825). However, a striking reduction was observed in all-cause mortality in non-ischemic patients treated with amlodipine. There were 45 deaths in the amlodipine group and 74 deaths in the placebo group, with overall a 46% reduction in the risk of death (95% Cl for the hazard ratio 0.373 to 0.783), which was statistically significant (p=0.0012).

In this double-blind study, the clinical efficacy and safety of amlodipine was evaluated in 1153 patients with chronic heart failure. All patients received background therapy with digoxin, diuretics and an angiotensin converting enzyme inhibitor. Overall, amlodipine proved to be safe in patients with NYHA III and IV heart failure. There was no difference between amlodipine and placebo on the primary endpoint of combined morbid and fatal events. There was a positive trend (p=0.07) in favor of amlodipine in the secondary endpoint of all-cause mortality. Furthermore, there was a significant treatment-etiology interaction for both primary and secondary endpoints. In the ischemic etiology stratum amlodipine had no detrimental effects on primary and secondary endpoints. More importantly, however, amlodipine was found to have significant positive effects on both primary and secondary endpoints in patients with non-ischemic etiology. Amlodipine resulted in a significant reduction in combined morbid and fatal events as compared to placebo. There was a larger and even more striking benefit from drug on the secondary endpoint of all-cause mortality. Amlodipine caused a significant and substantial reduction in all-cause mortality, as compared to placebo. The dramatic reduction in primary and secondary endpoints with amlodipine are even more striking when it is noted that these effects are in addition to any and all benefits derived from the combination of angiotensin converting enzyme inhibitors, digoxin, diuretic, or any component thereof.

What is claimed is:

1. A method for reducing morbidity and/or reducing the risk of mortality in a mammal with congestive heart failure due to non-ischemic etiology, comprising administering to said mammal a non-ischemic congestive heart failure treating amount of a compound selected from the group consisting of amlodipine and pharmaceutically acceptable salts of amlodipine.

2. A method as defined in claim 1, wherein said mammal is a human.

3. A method as defined in claim 2, wherein said compound is the besylate salt of amlodipine.

4. A method as defined in claim 2, further comprising co-administering a diuretic.

5. A method as defined in claim 4, wherein said diuretic is selected from the group consisting of methyclothiazide, hydrochlorothiazide, torsemide, metolazone, furosemide, chlorthalidone, N-(5-sulfamoyl-1,3,4-thiadiazol-2-yl) acetamide, triamterene, chlorothiazide, indapamide, bumetanide, amiloride, spironolactone, bendroflumethiazide, benzthiazide, cyclothiazide, quinethazone, hydroflumethiazide, polythiazide, trichlormethiazide, and ethacrynic acid.

6. A method as defined in claim 2, further comprising co-administering digoxin.

7. A method as defined in claim 4, further comprising co-administering digoxin.

8. A method as defined in claim 5, further comprising co-administering digoxin.

9. A method as defined in claim 2, wherein administration is effected for longer than 16 weeks.

10. A method as defined in claim 9, wherein administration is effected for longer than six months.

\* \* \* \* \*